(12) United States Patent
Maeda et al.

(10) Patent No.: US 9,155,752 B2
(45) Date of Patent: Oct. 13, 2015

(54) LIVER FUNCTION-IMPROVING AGENT

(71) Applicant: UENO FINE CHEMICALS INDUSTRY, LTD., Osaka-shi, Osaka (JP)

(72) Inventors: Kazuhisa Maeda, Suita (JP); Toshinori Ito, Suita (JP); Hayato Urushima, Suita (JP); Junya Honda, Osaka (JP); Ryosuke Kawaura, Osaka (JP); Aya Kuretani, Osaka (JP)

(73) Assignee: UENO FINE CHEMICALS INDUSTRY, LTD., Osaka (JP)

( * ) Notice: Subject to any disclaimer, the term of this patent is extended or adjusted under 35 U.S.C. 154(b) by 0 days.

(21) Appl. No.: 13/903,354

(22) Filed: May 28, 2013

(65) Prior Publication Data

US 2013/0324484 A1    Dec. 5, 2013

(30) Foreign Application Priority Data

May 29, 2012  (JP) ................................ 2012-122255
Nov. 30, 2012  (JP) ................................ 2012-263122
Nov. 30, 2012  (JP) ................................ 2012-263134

(51) Int. Cl.
| | | |
|---|---|---|
| A61K 31/7032 | (2006.01) | |
| A23L 1/30 | (2006.01) | |
| A23L 2/52 | (2006.01) | |
| A23L 1/09 | (2006.01) | |
| A61K 9/00 | (2006.01) | |
| A61K 47/26 | (2006.01) | |
| A61K 9/20 | (2006.01) | |

(52) U.S. Cl.
CPC .............. *A61K 31/7032* (2013.01); *A23L 1/09* (2013.01); *A23L 1/30* (2013.01); *A23L 2/52* (2013.01); *A61K 9/0095* (2013.01); *A61K 47/26* (2013.01); *A23V 2002/00* (2013.01); *A61K 9/2018* (2013.01)

(58) Field of Classification Search
None
See application file for complete search history.

(56) References Cited

U.S. PATENT DOCUMENTS

| | | | |
|---|---|---|---|
| 3,940,481 | A | 2/1976 | Schiweck |
| 2010/0129333 | A1 | 5/2010 | Kawakami et al. |

FOREIGN PATENT DOCUMENTS

| | | | |
|---|---|---|---|
| CN | 101744865 A | | 6/2010 |
| EP | 1 553 100 A1 | | 7/2005 |
| JP | 59-225120 A | | 12/1984 |
| JP | 5-43470 A | | 2/1993 |
| JP | 11-209297 A | | 9/1999 |
| JP | 2001-226289 A | | 8/2001 |
| JP | 2005-179213 A | | 7/2005 |
| JP | 2005-179277 A | | 7/2005 |
| JP | 2008-24680 A | | 2/2008 |
| JP | 2008-247791 A | | 10/2008 |
| JP | 2009-263257 A | | 11/2009 |
| JP | 2010-105948 A | | 5/2010 |
| JP | 2010-248141 A | | 11/2010 |
| JP | 2011-201801 A | | 10/2011 |
| JP | 2011-201841 A | | 10/2011 |

OTHER PUBLICATIONS

Hosaka et al.—The Japanese Journal of Gastro-enterology, vol. 71(11), 1974, pp. 1166-1171.*
Kikuchi H et al; Hirosaki Medical Journal, vol. 26, No. 1, 1974, pp. 13-19.
Maranesi M et al; ACTA Vitaminologica et Enzymologica, vol. 6, No. 1, 1984, pp. 11-15.
WPI/Thomson, AN 2009-N99283, vol. 2009, No. 67, Sep. 16, 2009.
Hosaka H et al; Nihon Shokakibyo Gakkai Zashi=the Japanese Journal of Gastro-enterology, vol. 71, No. 11, 1974, pp. 1166-1171.
Extended European Search Report for corresponding Application No. 13169326.9 dated Jul. 18, 2013.
Medical Examination Guide 2010 for NASH/NAFLD, edited by the Japan Society of Hepatology, published on Dec. 18, 2010 by Bunkodo Co., Ltd.

* cited by examiner

*Primary Examiner* — Traviss C McIntosh, III
(74) *Attorney, Agent, or Firm* — Sughrue Mion, PLLC

(57) ABSTRACT

The present invention provides a liver function-improving agent or an inhibitor of fat accumulation in the liver, which contains maltitol as an active ingredient. The present invention also provides a medicament for the prevention and/or treatment of hepatic dysfunction, which contains maltitol as an active ingredient.

9 Claims, 3 Drawing Sheets

LIVER FUNCTION-IMPROVING AGENT

TECHNICAL FIELD

The present invention relates to a liver function-improving agent, which contains maltitol as an active ingredient, and a medicament for the prevention and/or treatment of hepatic dysfunction, which contains maltitol as an active ingredient.

BACKGROUND ART

Liver disease, in one typical example, develops and progresses as follows: (1) acute hepatitis develops mainly due to viral infection and drug allergy, (2) the acute hepatitis transitions to chronic hepatitis, and (3) the chronic hepatitis further progresses and transitions to liver cirrhosis or liver cancer. It is important to prevent liver diseases from becoming chronic. In addition, patients with alcoholic or non-alcoholic fatty liver associated with lifestyle-related diseases such as obesity and diabetes have been increasing in recent years.

Subjective symptoms are less in an early stage of liver diseases. Particularly, chronic hepatitis and liver cirrhosis are characterized by almost no early symptoms. Therefore, it is important to observe what kind of state the liver is now in by the inspection including blood tests at medical examinations. Aspartate aminotransferase (hereinafter referred to as AST) and alanine aminotransferase (hereinafter referred to as ALT) are each a test item that is most basic in a liver function test. Both AST and ALT are enzymes that are present in the organ cells and catalyze the transamination of amino acids. When the hepatocytes are destroyed due to damages such as inflammation, AST and ALT in the cells flow out into the blood, and blood levels of these escaped enzymes elevate. A normal value of blood AST is 12 to 40 IU/L and a normal value of blood ALT is 5 to 40 IU/L. In contrast, the blood ALT value in a patient with acute hepatocyte disorder may be 500 IU/L or more.

Fatty liver is a disease in which neutral fat accumulates in hepatocytes. When hepatocytes of a patient with fatty liver are viewed under a microscope, vacuoles containing fat droplets are observed. In many cases, AST value and ALT value of fatty liver patients are slightly higher than the normal values (2 to 4 times the normal value, or less). Fatty liver includes simple steatosis and steatohepatitis accompanied with fibrosis of the hepatocytes. It is often the case that an AST value and an ALT value in the steatohepatitis are high in comparison with those in simple steatosis.

Blood AST and ALT values are important indicators in the inspection of liver dysfunction, and an improvement of AST value and ALT value is needed in the prevention and treatment of various liver diseases.

Various medicaments for the prevention or improvement of liver dysfunction are known. As a medicament for the prophylaxis or treatment of viral hepatic disease, a therapeutic agent for hepatitis B or hepatitis C is known in addition to hepatitis virus vaccines. Known liver function-improving agents derived from natural products include an extract from cortex of *Mallotus japonicus* (Patent Document 1), lactoperoxidase (Patent Document 2), S2U type triglyceride (Patent Document 3), glutathione and turmeric (*Curcuma longa*) (Patent Document 4), isomaltulose (Patent Document 5), and Japanese apricot extract or a neutralization product of Japanese apricot extract for patients with viral hepatitis (Patent Document 6).

Insulin sensitizers, therapeutic agents for dyslipidemia, medicaments for liver, and angiotensin II1 receptor antagonists have been reported as effective for inhibiting fat accumulation in the liver (Non-Patent Document 1). Known agents which are derived from natural products and prevent fat accumulation in the liver include a high polymer polysaccharide substance MPS-80 (Patent Document 7), a hemicellulose obtained from corn bran and/or partially degraded product thereof for patients with alcoholic liver disease (Patent Document 8), a polysaccharide having a molecular weight of 400,000 or more derived from tea (Patent Document 9), a culture and/or bacterial cells of lactic acid bacteria belonging to *Lactobacillus gasseri* (Patent Document 10), olive or an extract thereof (Patent Document 11), barley bran or Cc-amylase treated product thereof (Patent Document 12), and bacterial cells of *Lactobacillus helveticus* (Patent Document 13).

PRIOR ART DOCUMENTS

Patent Documents

[Patent Document 1] JP H11-209297 A
[Patent Document 2] JP 2001-226289 A
[Patent Document 3] JP 2008-247791 A
[Patent Document 4] JP 2005-179213 A
[Patent Document 5] JP 2010-248141 A
[Patent Document 6] JP 2011-201841 A
[Patent Document 7] JP S59-225120 A
[Patent Document 8] JP H05-43470 A
[Patent Document 9] JP 2005-179277 A
[Patent Document 10] JP 2008-24680 A
[Patent Document 11] JP 2009-263257 A
[Patent Document 12] JP 2010-105948 A
[Patent Document 13] JP 2011-201801 A

Non-Patent Document

[Non-Patent Document 1] "Medical Examination Guide 2010 for NASH/NAFLD", edited by the Japan Society of Hepatology (Published on Dec. 18, 2010 by Bunkodo Co., Ltd.)

SUMMARY OF THE INVENTION

An object of the present invention is to provide a liver function-improving agent. Another object of the present invention is to provide an inhibitor of fat accumulation in the liver. A further object of the present invention is to provide a medicament useful for the prevention and/or treatment of hepatic dysfunction.

The present inventors have found that maltitol has an action of decreasing blood AST and ALT and improving liver function, and then completed the present invention.

The present invention provides a liver function-improving agent containing maltitol as an active ingredient (hereinafter also referred to as a "liver function-improving agent of the present invention").

The present invention also provides an inhibitor of fat accumulation in the liver, which contains maltitol as an active ingredient (hereinafter also referred to as a "fat accumulation inhibitor of the present invention").

The present invention also provides a medicament for the prevention and/or treatment of hepatic dysfunction, which contains maltitol as an active ingredient (hereinafter also referred to as a "medicament for the prevention/treatment of hepatic dysfunction of the present invention").

The present invention also provides a medicament for non-human animals, for the prevention and/or treatment of hepatic dysfunction in non-human animals, containing maltitol; a method of preventing and/or treating hepatic dysfunction in non-human animals, which comprises administering the medicament, or the liver function-improving agent of the present invention or the fat accumulation inhibitor of the present invention to non-human animals; a method of producing a functional food or drink, which comprises mixing or adding the liver function-improving agent of the present invention or the fat accumulation inhibitor of the present invention, with or to the food or drink; and use of the liver function-improving agent of the present invention or the fat accumulation inhibitor of the present invention for the production of supplements.

The present invention also provides a method of preventing and/or treating hepatic dysfunction, which comprises administering an effective amount of maltitol to a subject in need of the prevention and/or treatment of hepatic dysfunction (hereinafter also referred to as a "method of preventing/treating hepatic dysfunction of the present invention"); a method of improving liver function in a subject, which comprises administering an effective amount of maltitol to the subject whose liver function is decreased relative to a normal state (hereinafter also referred to as a "liver function-improving method of the present invention"); and a method of inhibiting fat accumulation in the liver of a subject, which comprises administering an effective amount of maltitol to the subject (hereinafter also referred to as a "fat accumulation-inhibiting method of the present invention").

The present invention also provides maltitol for use in the prevention and/or treatment of hepatic dysfunction.

The present invention also provides use of maltitol in the manufacture of a medicament for the prevention and/or treatment of hepatic dysfunction.

The present invention also provides use of maltitol in the manufacture of a liver function-improving agent; and use of maltitol in the manufacture of an inhibitor of fat accumulation in the liver.

The present invention also provides maltitol for use in the manufacture of a medicament for the prevention and/or treatment of hepatic dysfunction; maltitol for use in the manufacture of a liver function-improving agent; and maltitol for use in the manufacture of an inhibitor of fat accumulation in the liver.

DETAILED DESCRIPTION OF THE INVENTION

Figure 1:
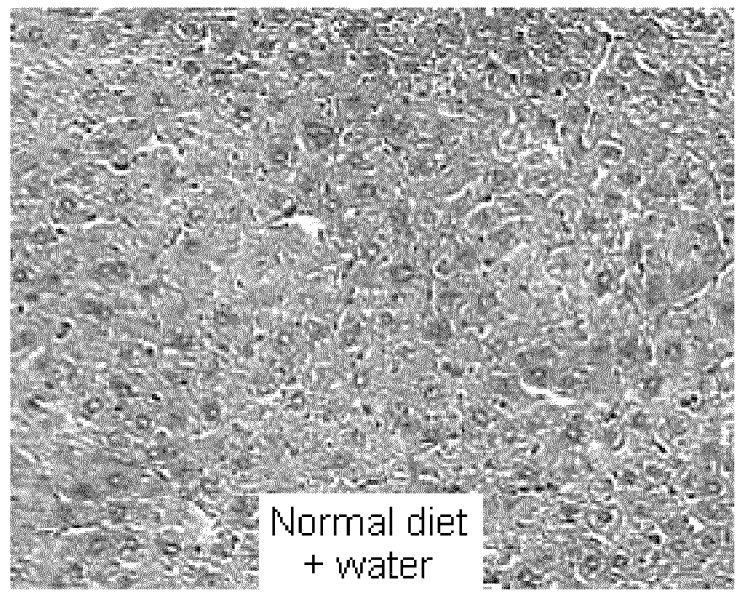
FIG. 1 shows the result of microscopic observation of the liver tissue stained with hematoxylin-eosin (HE) in mice of group 1 (normal diet+distilled water).

Maltitol, which is an active ingredient of a liver function-improving agent, a fat accumulation inhibitor, and a medicament for the prevention/treatment of hepatic dysfunction of the present invention, may be either produced by a known production method or commercially available maltitol products. The method of producing maltitol includes, for example, a method in which a starch syrup containing maltose is hydrogenated by subjecting it to high pressure catalytic reduction in the presence of a catalyst, followed by purification and concentration. Examples of commercially available maltitol products include Hydrogenated Starch Hydrolysates Syrups MU-45, MU-50, and MU-65, and Hydrogenated Maltose Syrup MU-75 and Whole Crystalline Maltitol Ueno (Maltitol Powder) manufactured by UENO FINE CHEMICALS INDUSTRY, LTD.

The properties of maltitol used in the present invention may be either liquid or solid, and maltitol may be, for example, powdered maltitol or crystalline maltitol produced from liquid maltitol by a known powderization or crystallization method. The properties of maltitol to be used can be appropriately selected depending on the objective dosage form.

With respect to the purity of maltitol used in the present invention, liquid maltitol preferably has a purity of 45% or more. Powdered maltitol preferably has a purity of 80% or more, more preferably 85% or more, and still more preferably 88% or more.

Both a liver function-improving agent and a fat accumulation inhibitor of the present invention contain maltitol as an active ingredient. The liver function-improving agent and the fat accumulation inhibitor may further contain excipients and the like, as long as they do not interfere with the liver function-improving effect or fat accumulation inhibitory effect exerted by maltitol. There is no particular limitation on the proportion of maltitol in the liver function-improving agent or in the fat accumulation inhibitor of the present invention. For example, the liver function-improving agent or the fat accumulation inhibitor of the present invention can contain maltitol in the proportion of 40% by weight or more, 45% by weight or more, 50% by weight or more, 60% by weight or more, 70% by weight or more, 80% by weight or more, 85% by weight or more, 90% by weight or more, 95% by weight or more, or 98% by weight or more. Alternatively, the liver function-improving agent or the fat accumulation inhibitor of the present invention may consist only of maltitol. In one embodiment, maltitol may be the sole active ingredient in the liver function-improving agent or in the fat accumulation inhibitor of the present invention.

The medicament for the prevention/treatment of hepatic dysfunction of the present invention contains maltitol as an active ingredient, as is the case with the liver function-improving agent and the fat accumulation inhibitor of the present invention.

The proportion of maltitol to be contained in the medicament for the prevention/treatment of hepatic dysfunction of the present invention as an active ingredient can be appropriately determined depending on the objective dosage form and the like, and may be usually from about 1 to 98% by weight, preferably from about 2 to 95% by weight, and more preferably from about 3 to 90% by weight, based on the whole amount of the medicament. In one embodiment, maltitol may be the sole active ingredient in the medicament for the prevention/treatment of hepatic dysfunction of the present invention.

In a preferred embodiment of the present invention, the prevention and/or treatment of hepatic dysfunction is/are achieved through any one or more of inhibition of fat accumulation in the liver, inhibition of hepatic fibrosis, and inhibition of hepatic inflammation.

The term "hepatic dysfunction" refers to a state in which the liver function is decreased relative to a normal state. In general, hepatic dysfunction is a state characterized in that any one or more measurement values of inspection items for liver function (e.g. levels of blood AST, ALT, γ-GTP, ALP, TTT, ZTT, total bilirubin, total protein, albumin, LDH (lactate dehydrogenase), choline esterase and the like) are deviated from the range of normal values (reference values). The reference value of liver function test may vary depending on medical inspection institutions, inspection methods, measurement equipments, reagents to be used and the like, but the reference values listed in, for example, "Program About Standard Medical Examination/Health Instruction (final version)" (Ministry of Health, Labour and Welfare), "Commentary on Clinical Inspection Items" (Web page of Mitsubishi Chemical Medience Corporation), and "Hepatic diseases—Basic knowledge in era when the diseases can be cured" (written by Sumio Watanabe, Iwanami Shoten, Publishers) can be used or referenced.

In one aspect, the medicament for the prevention/treatment of hepatic dysfunction of the present invention is based on a newly found action of maltitol, i.e., an action of decreasing blood AST and ALT. In one embodiment, hepatic dysfunction that is an indication of the medicament for the prevention/treatment of hepatic dysfunction of the present invention is characterized in that blood AST value and/or ALT value deviate from a range of normal values (e.g. AST of 12 to 40 IU/L and ALT of 5 to 40 IU/L).

In the present specification, "treatment" of hepatic dysfunction also includes the inhibition of the progression of hepatic dysfunction in a patient already suffering from hepatic dysfunction. For example, the "treatment" includes the inhibition of the further progression of hepatic dysfunction from mild chronic liver disease such as fatty liver, and the inhibition of further fat accumulation in the liver of a patient already suffering from fatty liver.

A way of administration of the medicament for the prevention/treatment of hepatic dysfunction of the present invention may be either of oral administration or parenteral administration. Timing of administration of the medicament is not particularly limited and may be either of before meal, during meal, after meal, or between meals. For example, the medicament is preferably administered at any time of before meal, during meal, after meal, or between meals, wherein the meal contains a fat in an amount of 10% by weight or more. In the case of oral administration, the medicament is especially preferably administered after meal or multiple times daily in small amounts, in terms of avoiding the adverse drug reaction of diarrhea due to large amounts of maltitol. Wherein, although "meal(s)" generally refer(s) to eating a food as a daily habit to take nutrients necessary for living (eating and drinking action) or to the food or drink taken, the term "meal(s)" used herein refer(s) to a set of foods or drinks taken in one eating or drinking action.

The dosage of the medicament for the prevention/treatment of hepatic dysfunction of the present invention is appropriately selected depending on conditions such as severity of hepatic dysfunction, severity of other diseases, age, sex and the like. In one embodiment, the medicament may be administered in an amount that can reduce values of AST and ALT, each of which is an indicator of hepatic dysfunction, to a normal value or a value close to the normal value (hereinafter also referred to as an "effective amount for reduction of AST/ALT"). In another embodiment, the medicament is administered in an amount that can inhibit fat accumulation in the liver (hereinafter also referred to as an "effective amount for inhibition of fat accumulation"), or in an amount that can inhibit hepatic fibrosis (hereinafter also referred to as an "effective amount for inhibition of hepatic fibrosis"), or in an amount that can inhibit hepatic inflammation (hereinafter also referred to as an "effective amount for inhibition of hepatic inflammation"). These effective amounts can be appropriately determined using the method well-known to those skilled in the art (including various non-clinical and/or clinical studies).

With respect to the medicament for the prevention/treatment of hepatic dysfunction of the present invention, the effective amount (an effective amount for reduction of AST/ALT, an effective amount for inhibition of fat accumulation, an effective amount for inhibition of hepatic fibrosis, or an effective amount for inhibition of hepatic inflammation) of maltitol may be administered in a single dose or separately administered in multiple doses at intervals. In the case of oral administration, the medicament is preferably administered separately in multiple doses in terms of laxative property. If the medicament is separately administered in multiple doses, total amount of maltitol administered per day may be the effective amount described above and the medicament is preferably administered in accordance with the number of meals.

In the present specification, the "prevention and/or treatment of hepatic dysfunction" includes a prevention and/or treatment of various liver diseases exhibiting hepatic dysfunction, such as viral liver disease, drug-induced liver disease, alcoholic fatty liver and non-alcoholic fatty liver, alcoholic steatohepatitis and non-alcoholic steatohepatitis, liver cirrhosis, liver cancer and the like. The liver disease to which the medicament for the prevention/treatment of hepatic dysfunction of the present invention may be applied is preferably alcoholic fatty liver, non-alcoholic fatty liver, alcoholic steatohepatitis, non-alcoholic steatohepatitis, liver cirrhosis, and liver cancer, all of which are deeply related to AST values and/or ALT values exceeding the normal values. In one embodiment, the liver disease to which the medicament for the prevention/treatment of hepatic dysfunction of the present invention may be applied is non-alcoholic steatohepatitis.

It was also confirmed that maltitol had an effect to inhibit the fat accumulation in the liver. Therefore, in one embodiment, the medicament for the prevention/treatment of hepatic dysfunction of the present invention is administered to a person suffering from alcoholic or non-alcoholic fatty liver or alcoholic or non-alcoholic steatohepatitis, preferably to a person suffering from non-alcoholic fatty liver or non-alcoholic steatohepatitis which has a great need for dieting.

The medicament for the prevention/treatment of hepatic dysfunction of the present invention can be used for the prevention and/or treatment of hepatic dysfunction in a person suffering from a disease whose progression to liver disease is of a problem, such as obesity, diabetes, dyslipidemia, hyperlipidemia, hypertension, impaired glucose tolerance, metabolic syndrome, fat dystrophy, β-lipoprotein deficiency, Weber-Christian disease, Wolman disease, acute fatty liver of pregnancy, Wilson's disease, Indian childhood cirrhosis, etc. The medicament described above is preferably used for the prevention and/or treatment of hepatic dysfunction in a person suffering from obesity and diabetes that have a great need for dieting, among persons suffering from such diseases.

Furthermore, the medicament for the prevention/treatment of hepatic dysfunction of the present invention can be administered to healthy individuals to effectively prevent hepatic dysfunction.

The medicament for the prevention/treatment of hepatic dysfunction of the present invention can be used in various dosage forms by adding further components such as excipients, stabilizers, preservatives, buffering agents, corrigents, suspending agents, emulsifiers, flavoring agent, solubilizers, coloring agents, and viscous agents in addition to maltitol, as long as they do not interfere with the effect of the prevention/ treatment of hepatic dysfunction exerted by maltitol.

The dosage forms of the medicament for the prevention/ treatment of hepatic dysfunction of the present invention include tablets (orally-disintegrating tablets, chewable tablets, effervescent tablets, dispersible tablets, and soluble tablets), capsules, granules (effervescent granules), powders, liquids and solutions for oral administration (elixirs, suspensions, emulsions, and lemonades), syrups (preparations for syrups), jellies for oral administration, tablets for oromucosal application (troches/lozenges, sublingual tablets, buccal tablets, mucoadhesive tablets, and medicated chewing gums), sprays for oromucosal application, semi-solid preparations for oromucosal application, preparations for gargles, injections (parenteral infusions, implants/injections, and prolonged release injections), dialysis agents (peritoneal dialysis agents and hemodialysis agents), inhalations (dry powder inhalers, inhalation solutions, and metered-dose inhalers), suppositories for rectal application, semi-solid preparations for rectal application, enemas for rectal application, ophthalmic preparations, ophthalmic ointments, ear preparations, nasal preparations (nasal dry powder inhalers and nasal solutions), tablets for vaginal use, suppositories for vaginal use, solid dosage forms for cutaneous application (powders for cutaneous application), liquids and solutions for cutaneous application (liniments and lotions), sprays for cutaneous application (aerosols for cutaneous application and pump sprays for cutaneous application), ointments, creams, gels, patches (tapes/plasters and cataplasms/gel patches), etc. Among these dosage forms, in terms of easy delivery to the liver, tablets, capsules, granules, powders, liquids and solutions for oral administration, syrups, jellies for oral administration, tablets for oromucosal application, sprays for oromucosal application, semi-solid preparations for oromucosal application, preparations for gargles, injections, dialysis agents, inhalations, suppositories for rectal application, semi-solid preparations for rectal application, and enemas for rectal application are preferable, and in terms of being easy to administer orally, tablets, capsules, granules, powders, liquids and solutions for oral administration, syrups, jellies for oral administration, tablets for oromucosal application, sprays for oromucosal application, semi-solid preparations for oromucosal application and preparations for gargles are more preferable.

The medicament for the prevention/treatment of hepatic dysfunction of the present invention can also be used in dosage forms in which maltitol is added to preparations related to crude drugs such as extracts, pills, spirits, infusions and decoctions, teabags, tinctures, aromatic waters, and fluid extracts. These dosage forms are appropriately selected depending on conditions such as severity of hepatic dysfunction, severity of other diseases, age, sex, and the like.

The medicament for the prevention/treatment of hepatic dysfunction of the present invention can further contain other drugs having liver function-improving effects. These drugs include, for example, insulin sensitizers (thiazolidine derivatives, biguanide drugs, etc.), antioxidants (vitamin E, vitamin C, eicosapentaenoic acid, betaine, N-acetylcysteine, etc.), antidyslipidemic agents (fibrate-based drugs, HMG-CoA reductase inhibitors, probucol, etc.), liver protection drugs (ursodeoxycholic acid, glycyrrhizin preparation, Shosaikoto, taurine, etc.), angiotensin II type 1 receptor blockers (losartan, etc.), and the like.

The medicament for the prevention/treatment of hepatic dysfunction of the present invention can further contain natural products or naturally derived substances having liver function-improving effects. These natural products or naturally derived substances include, for example, animal liver, animal liver-derived substances (shark liver oil, peptides obtained by enzymatic degradation of pig liver, etc.), policosanol, arrowroot (*Pueraria lobata*) flower, L-ornithine, *Ampelopsis glandulosa* var. *heterophylla* or substances derived from *Ampelopsis glandulosa* var. *heterophylla* (e.g. resveratrol), walnut, walnut-derived substances (e.g. walnut polyphenols), α-lipoic acid, artichoke (*Cynara scolymus*), astaxanthin, aspartic acid, alanine, yellow dock (Japanese name: Nagabagishigishi (curled dock); Scientific name: *Rumex crispus*), turmeric, oyster, zedoary (*Curcuma zedoaria*), guarana (*Paullinia cupana*), licorice (*Glycyrrhiza*), wild turmeric (*Curcuma aromatica*), chlorella, glycyrrhizin, Korean ginseng (*Panax ginseng*), coffee, sesame lignan, S-adenosylmethionine (SAMe), corbicula, cysteine, silymarin, spirulina, chancapiedra (Japanese name: Kidachikomikansou; Scientific name: *Phyllanthus niruri*), Denshichi carrot (*Panax notoginseng*), fenugreek (Japanese name: Koroha; Scientific name: *Trigonella foenum-graecum*), sesamin, taurine, dandelion (Taraxacum), fucoidan, milk thistle (*Silybum marianum*), lactoferrin, raffinose, bracket fungus (*Ganoderma lucidum*), lecithin, royal jelly, etc.

Maltitol can also be used to prevent and/or treat hepatic dysfunction in non-human animals. Therefore, in one embodiment of the present invention, a medicament for non-human animals containing maltitol for the prevention and/or treatment of hepatic dysfunction in non-human animals (hereinafter also referred to as a "medicament for non-human animals of the present invention") is provided. In addition, a method of preventing and/or treating hepatic dysfunction in non-human animals, which includes administering the medicament for non-human animals, the liver function-improving agent or the fat accumulation inhibitor of the present invention to the non-human animals, is also provided. Examples of non-human animals include livestock such as cattle, horses, pigs, sheep, goats and chickens; animals that are reared as pets such as dogs and cats, and the like.

Amounts of maltitol contained in the medicament for non-human animals of the present invention; a way of administration, timing of administration, dosage, and dosage forms of the medicament; other drugs, natural products and naturally derived substances that can be used in combination with maltitol in the medicaments; and a way of administration, timing of administration, dosage and the like when a liver function-improving agent or a fat accumulation inhibitor of the present invention is administered to non-human animals are same as those described above regarding "the medicament for the prevention/treatment of hepatic dysfunction of the present invention".

The liver function-improving agent or the fat accumulation inhibitor of the present invention can also be used as food additives. Therefore, by mixing or adding the liver function-improving agent or the fat accumulation inhibitor of the present invention to food or drink, a functional food or drink for improving liver function, characterized by improvement (reduction) of blood AST value and blood ALT value, or a functional food or drink for inhibiting fat accumulation in the liver can be provided. By using as a component the liver function-improving agent or the fat accumulation inhibitor of the present invention, supplements that improve liver function or inhibit fat accumulation in the liver can also be manufactured. In this case, excipients and the like can be appropriately incorporated depending on the dosage forms of supplements to be manufactured.

Examples of the subject to which the method of preventing/ treating hepatic dysfunction of the present invention is applied include humans and non-human animals, for example, livestock such as cattle, horses, pigs, sheep, goats and chickens; and animals that are reared as pets such as dogs and cats.

In one embodiment of the present invention, maltitol is provided as a solution containing it, or as a food or drink to which the maltitol has been added. In one embodiment, a medicament for the prevention/treatment of hepatic dysfunction, a medicament for non-human animals, a liver function-improving agent, and a fat accumulation inhibitor of the present invention can be in the form of a solution containing maltitol, or a form of food or drink to which maltitol has been added. Examples of such form of the solution include liquids and solutions for oral administration, preparations for gargles, injections, enemas for rectal application, ophthalmic preparations, nasal solutions, liquids and solutions for cutaneous application, and the like.

EXAMPLES

The present invention will be further described below by way of Examples.

Test Example 1

(1) Test Animal

Eight-week-old C57BL/6 male mice (CLEA Japan, Inc.) were divided at random into groups (each group: four animals) and then used.

(2) Diet

As a normal diet, solid diet MF (lipid component 5.3%, manufactured by Oriental Yeast Co., Ltd.) was used. As a high-fat diet, solid diet High Fat Diet 32 (lipid component 32.0%, manufactured by CLEA Japan, Inc.) was used.

(3) Preparation of Sample

As a sample water, 2.5% by weight of aqueous sucrose solution, 2.25% by weight of aqueous maltitol solution, and 4.5% by weight of aqueous maltitol solution obtained by respectively dissolving, as a test substance, sucrose (manufactured by Wako Pure Chemical Industries, Ltd.) and maltitol (Whole Crystalline Maltitol Ueno 60M, having maltitol purity of 90%, manufactured by Ueno Fine Chemicals Industry, Ltd.) in distilled water were used. Distilled water was used as a negative sample. The sample water was administered by making it available ad libitum and the amount of sample water intake was recorded. The dose of sucrose per day calculated from the concentration of the sample water and the water intake was 3 g per 1 kg of body weight. The dose of maltitol per day calculated in the same manner as above was 2.7 g per 1 kg of body weight in mice receiving 2.25% aqueous maltitol solution, and 4.5 g per 1 kg of body weight in mice receiving 4.5% aqueous maltitol solution.

(4) Test Method

The diet and the sample water (test substance aqueous solution or distilled water) listed in Table 1 were administered to mice in each group, and the animals were fed for 8 weeks. After 8-week test feeding, pentobarbital of 0.5 mg/10 g of body weight was intraperitoneally administered to mice, and blood was collected from the tail vein under deep anesthesia. With respect to the serum from the collected blood sample of mice, blood AST value and blood ALT value which are each an indicator of liver function were measured using a Transaminase C-II Test Wako Kit (Wako Pure Chemical Industries, Ltd.).

Further, by using Precision Xceed β-Ketone Measuring Electrode (manufactured by Abbott Japan Co., Ltd.), ketone bodies value in blood, which is an indicator of fat burning in the liver, was measured.

TABLE 1

| Group constitution | | |
|---|---|---|
| Group No. | Diet | Sample water |
| Group 1 | Normal diet | Distilled water |
| Group 2 | High fat diet | Distilled water |
| Group 3 | High fat diet | 2.5% Aqueous sucrose solution |
| Group 4 | High fat diet | 2.25% Aqueous maltitol solution |
| Group 5 | High fat diet | 4.5% Aqueous maltitol solution |

(5) Evaluation of Blood AST Value, Blood ALT Value, and Blood Ketone Bodies Value A significant difference test by the t-test method was performed on blood AST values, blood ALT values, and blood ketone bodies values were evaluated by performing significant difference tests on these values via t-test.

(6) Results

As a result of the blood test, blood AST values showed a tendency to be decreased in group 4 (high fat diet+2.25% aqueous maltitol solution) relative to group 3 (high fat diet+ 2.5% aqueous sucrose solution). The blood AST value in group 5 (high fat diet+4.5% aqueous maltitol solution) was decreased to a level equivalent to that in group 1 (normal diet+distilled water) which was a normal control group. In addition, with respect to the blood ALT values, the similar decreasing tendency was observed as for the blood AST values. In particular, an effect of significantly decreasing the blood ALT value was observed in group 5 when compared to group 3. On the other hand, the blood ketone bodies values were increased in group 4 and group 5 relative to group 3, and in particular, a significant improvement effect was observed in group 4 in comparison with group 3. The evaluation results of blood AST values and blood ALT values are shown in Table 2 and the evaluation result of blood ketone bodies values is shown in Table 3.

TABLE 2

Evaluation result of blood AST value and blood ALT value (Unit: IU/L)

| | Blood AST value (Mean ± Standard error) | Significant difference | Blood ALT value (Mean ± Standard error) | Significant difference |
|---|---|---|---|---|
| Group 1 | 57 ± 7 | | 10 ± 0 | |
| Group 2 | 127 ± 38 | | 38 ± 16 | |
| Group 3 | 244 ± 107 | | 50 ± 12 | |
| Group 4 | 205 ± 77 | | 41 ± 14 | |
| Group 5 | 54 ± 3 | | 11 ± 1 | * |

* The asterisk (*) in the column of significant difference indicates that a significant difference was observed at 1% level of significance relative to group 3.

TABLE 3

Evaluation result of blood ketone bodies value

| | Blood ketone bodies value (Mean ± Standard error) | (Unit: mmol/L) Significant difference |
|---|---|---|
| Group 1 | 0.38 ± 0.10 | |
| Group 2 | 0.13 ± 0.05 | |
| Group 3 | 0.08 ± 0.03 | |
| Group 4 | 0.20 ± 0.04 | * |
| Group 5 | 0.18 ± 0.05 | |

* The asterisk (*) in the column of significant difference indicates that a significant difference was observed at 1% level of significance relative to group 3.

Test Example 2

The following test was carried out in the same manner as in Test Example 1 for (1) test animal, (2) diet, and (3) preparation of sample.

(4) Test Method

The diet and the sample water (test substance aqueous solution or distilled water) listed in Table 1 were administered to mice in each group and the animals were fed for 8 weeks. After 8-week test feeding, pentobarbital of 100 mg/kg of body weight was intraperitoneally administered to mice, and the mice were euthanized, and then liver was excised.

(5) Evaluation of Fat Vacuoles in Hepatocytes

The liver tissue excised from mice was stained with hematoxylin-eosin (HE) and a specimen observation under a microscope was carried out. Moreover, the results of microscopic observation were analyzed by the following method and a significant difference was evaluated by the t-test.
[Analysis Method of Microscopic Observation Results]
Using HS All-in-One fluorescence microscope BZ-9000 (Keyence Corporation), four areas per mouse were photographed at random in a field of vision at 400-fold magnification, wherein the areas do not include any sites such as blood vessel that may affect the results. This photographing was performed for four mice per group to obtain 16 microscopic images in total per group. At first, stained parts such as cytoplasm and nucleus in hepatocytes were selected by the image analysis. Then fat vacuole parts were selected by color inversion and the number of pixels for the selected fat vacuole parts was considered as a fat vacuole area. In the analysis, Dynamic Cell Count software accompanying fluorescence microscope BZ-9000 was used.

(6) Results

Figure 2:
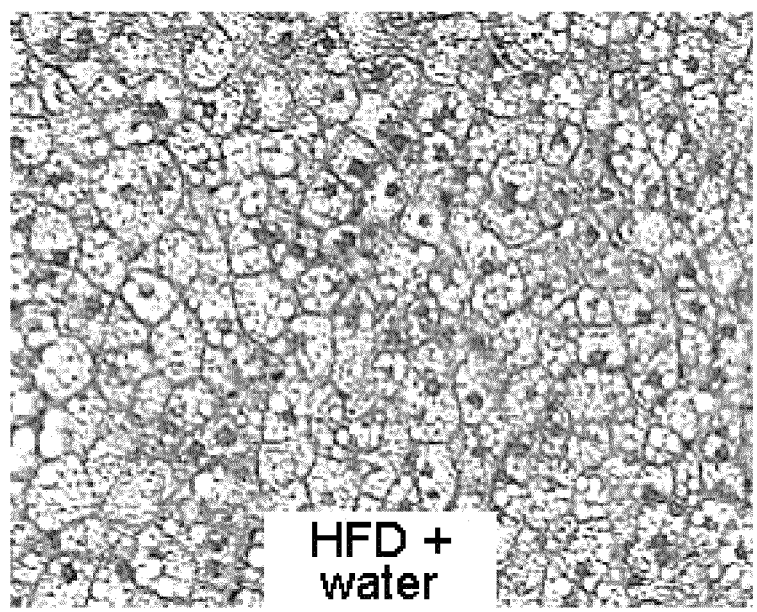
FIG. 2 shows the result of microscopic observation of the liver tissue stained with hematoxylin-eosin (HE) in mice of group 2 (high-fat diet+distilled water).
Figure 3:
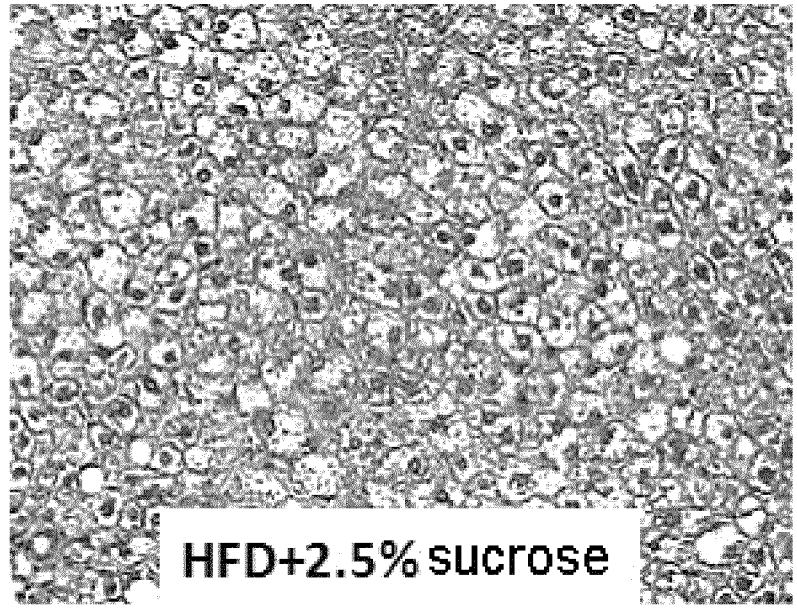
FIG. 3 shows the result of microscopic observation of the liver tissue stained with hematoxylin-eosin (HE) in mice of group 3 (high-fat diet+2.5% aqueous sucrose solution).
Figure 4:
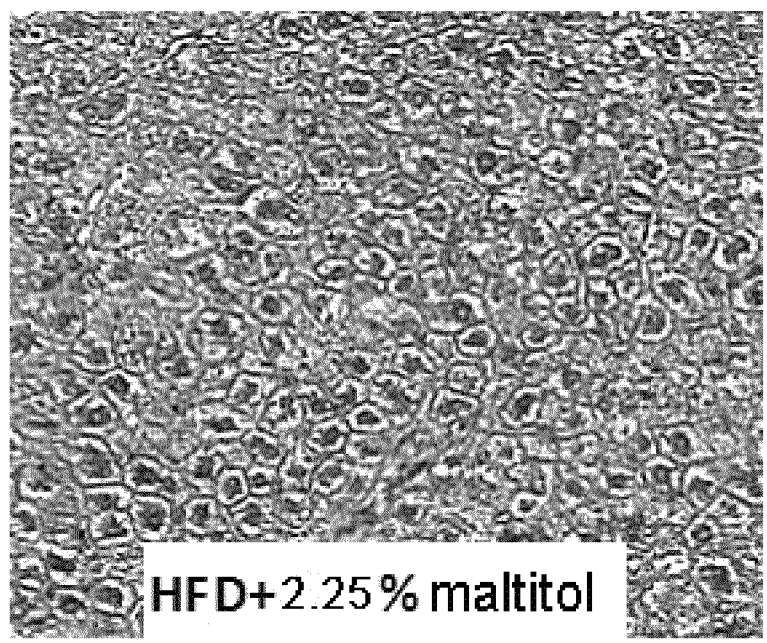
FIG. 4 shows the result of microscopic observation of the liver tissue stained with hematoxylin-eosin (HE) in mice of group 4 (high-fat diet+2.25% aqueous maltitol solution).
Figure 5:
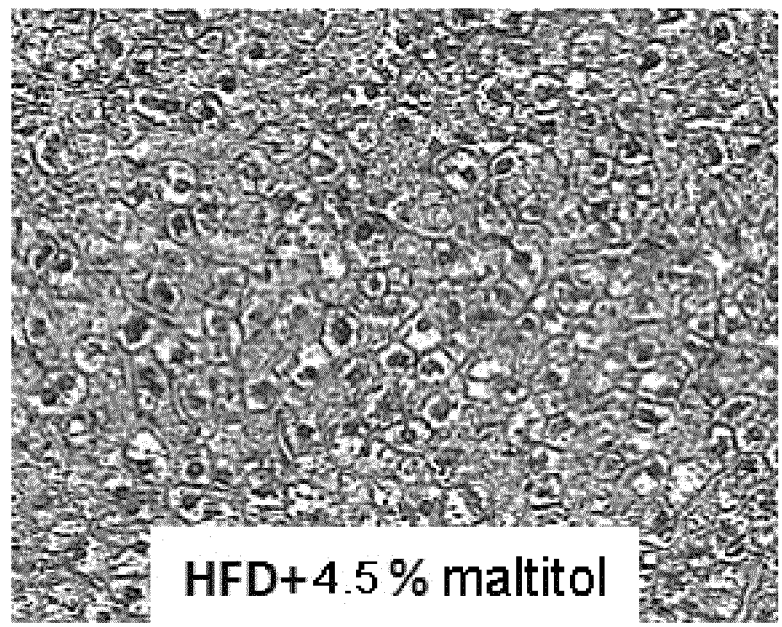
FIG. 5 shows the result of microscopic observation of the liver tissue stained with hematoxylin-eosin (HE) in mice of group 5 (high-fat diet+4.5% aqueous maltitol solution).

In the microscopic observation, fat that has accumulated in hepatocytes is not stained with HE, and is observed as white fat vacuoles. Many fat vacuoles were observed in group 2 (high fat diet+distilled water) as a control group for fatty liver, whereas few fat vacuoles were observed in group 4 (high fat diet+2.25% aqueous maltitol solution) and group 5 (high fat diet+4.5% aqueous maltitol solution). In addition, in group 4 and group 5, the fat vacuole area was significantly smaller than that in group 2. On the other hand, in group 3 (high fat diet+2.5% aqueous sucrose solution), reduction of the fat vacuoles is limited and an effect of significantly reducing the fat vacuole area in comparison with group 2 was not observed. The microscopic observation results are shown in FIGS. 1 to 5 and the evaluation result of fat vacuole area is shown in Table 4.

TABLE 4

Result of histological evaluation

| | Fat vacuole area (Mean ± Standard error) | (Unit: pixel) Significant difference |
|---|---|---|
| Group 1 | 179425 ± 12509 | |
| Group 2 | 386311 ± 26923 | |
| Group 3 | 306930 ± 28549 | No |
| Group 4 | 256145 ± 29037 | Yes |
| Group 5 | 264982 ± 16387 | Yes |

* Column of significant difference represents the presence or absence of a significant difference at 1% level of significance relative to group 2.

Test Example 3

(1) Preparation of Diet

A solid diet CE-2 (lipid 4.6% by weight, manufactured by CLEA Japan, Inc.) was used as a normal diet. A solid diet, High Fat Diet 32 (lipid 32.0% by weight, sucrose 6.75% by weight, manufactured by CLEA Japan, Inc.), was used as a sucrose-containing high fat diet. As a maltitol-containing high-fat diet, a special diet (lipid 32.0% by weight, maltitol 6.08% by weight; manufactured by CLEA Japan, Inc.) obtained by replacing the total amount (6.75% by weight) of sucrose in a solid diet, High Fat Diet 32, with powdered maltitol (Whole Crystalline Maltitol Ueno 60M (purity of maltitol: 90%), manufactured by Ueno Fine Chemicals Industry Ltd.) was used.

(2) Preparation of Drinking Water

Sodium hypochlorite (PURELOX-S, manufactured by OYALOX Co., Ltd.) was added to pure water prepared by Elix-UV pure water producing apparatus, to a final concentration of 0.00009%, so that pure water for use in the test was obtained. An aqueous maltitol solution was prepared by dissolving powdered maltitol (Whole Crystalline Maltitol Ueno 60M (purity of maltitol: 90%), manufactured by Ueno Fine Chemicals Industry Ltd.) in pure water to a concentration of 1.8% (weight/volume). The purity of maltitol in the aqueous maltitol solution was 1.62%.

(3) Test Animal

Twenty-one female SPF mice (C57BL/6J, produced by CLEA Japan, Inc.) on day 14 of pregnancy were purchased and acclimation was performed. All animals were allowed to make a natural birth and a born male was used to produce a model. In addition, the weaning was at 4 weeks after birth.
Production of NASH Mouse:
Streptozotocin (Sigma-Aldrich Japan K.K.) was adjusted to a concentration of 10 mg/mL with a physiological saline solution (manufactured by Otsuka Pharmaceutical Factory, Inc.) and the solution was subcutaneously administered once to the back of 2-day-old male mice at a dose of 20 μL/mouse (200 μg/mouse). Afterwards, the mother animal took care of the baby until weaning. The weaning was on day 28±2 after birth.
Adjustment of Children Born
After administration of streptozotocin, the children born were distributed without considering the litter so that the numbers of nursed children per a mother animal are equal. With respect to male individuals receiving no streptozotocin, the children born were distributed within a week after birth without considering the litter so that the numbers of nursed children per a mother animal are equal.

(4) Feeding Method

Feeding Conditions (Up to 4 Weeks of Age):

A normal diet was supplied ad libitum to both mother animals and child animals from animal arrival day to weaning day. The child animals were weaned at 4 weeks after birth.

Feeding Conditions (from 4 Weeks of Age to the Day Before 5 Weeks of Age):

After the weaning, a normal diet was supplied ad libitum to animals receiving no streptozotocin (normal mice (group S1 and group 1)), and a sucrose-containing high fat diet was supplied ad libitum to animals receiving streptozotocin (NASH mice (group S2, group 2, group 3, and group 4).

Feeding Conditions (from 5 Weeks of Age to 8 Weeks of Age):

A normal diet was supplied ad libitum to normal mice (group 1). With respect to NASH mice, a sucrose-containing high fat diet was supplied ad libitum to the sucrose group (group 2), and a maltitol-containing high fat diet was supplied ad libitum to the maltitol-low dose group (group 3) and the maltitol-high dose group (group 4).

An aqueous maltitol solution was supplied ad libitum only to the maltitol-high dose group (group 4) of 5 to 8 weeks of age, and pure water was supplied ad libitum to the groups other than group 4 of 5 to 8 weeks of age. The group constitution is shown in Table 5.

TABLE 5

Group constitution

| | Feeding (4 to 5 weeks of age) | | Feeding (5 to 8 weeks of age) | |
|---|---|---|---|---|
| Group No. | Diet | Water | Diet | Water |
| Group S1 | Normal | Pure water | | |
| Group S2 | HFD32 (Sucrose 6.75%) | Pure water | | |
| Group 1 | Normal | Pure water | Normal | Pure water |
| Group 2 | HFD32 (Sucrose 6.75%) | Pure water | HFD32 (Sucrose 6.75%) | Pure water |
| Group 3 | HFD32 (Sucrose 6.75%) | Pure water | HFD32-M (Maltitol 6.08%) | Pure water |
| Group 4 | HFD32 (Sucrose 6.75%) | Pure water | HFD32-M (Maltitol 6.08%) | Aqueous maltitol solution 1.62% |

* Normal: Normal diet
HFD32: Sucrose-containing high fat diet
HFD32-M: Maltitol-containing high fat diet Six male animals per group were assigned to groups S1 and S2, reared up to 5 weeks of age, and then necropsied. Eight male animals per group were assigned to groups 1, 2, 3 and 4, reared up to 8 weeks of age, and then necropsied.

At scheduled necropsy of the animals of 5 or 8 weeks of age, all individuals were anesthetized with diethyl ether (manufactured by Sigma-Aldrich Japan K.K.) and a needle through which heparin sodium (Novo Heparin Injection 1000, manufactured by Mochida Pharmaceutical Co., Ltd.) had been passed was punctured to the heart to aspirate the whole blood, leading to euthanasia, followed by harvest of the organ.

(5) Weighing of Liver

With respect to all animals at scheduled necropsy, the liver tissue collected was washed with a physiological saline solution and weighed using an electronic balance (AUW22D type, manufactured by Shimadzu Corporation).

(6) Oil Red Staining (Fat Accumulation Area %)

With respect to animals of 5 or 8 weeks of age at scheduled necropsy, the left outer lobe of the liver was immersed in a neutral formalin solution (manufactured by Wako Pure Chemical Industries, Ltd.) for fixation at room temperature for 24 hours, subjected to sucrose substitution, embedded in a tray for cryosection (CRYO DISH manufactured by Shoei Works Co., Ltd.) filled with O.C.T. compound (manufactured by Sakura Finetek Japan Co., Ltd.), immediately frozen with liquid nitrogen, and preserved at $-80°$ C. for oil red staining.

Using a section that was subjected to oil red staining according to a conventional method, images of 5 fields of vision per section were taken in a field of vision centered on central veins at 200-fold magnification. The oil red-positive area ratio (%) was calculated using Image J software (National Institute of Health, Bethesda, Md.) based on the images taken, and the normal group (group 1) and the test substance-administered groups (groups 3 and 4) were respectively compared to the sucrose group (group 2).

(7) Sirius Red Staining (Fibrosis Area %)

With respect to animals of 8 weeks of age at scheduled necropsy, the left outer lobe of the liver was immersed in Bouin's fixative solution (manufactured by Sigma-Aldrich Japan K.K.) for fixation at room temperature for 24 hours, and embedded in paraffin for Sirius Red staining.

Using a section that was subjected to Sirius Red staining according to a conventional method, images of 5 fields of vision per section were taken in a field of vision centered on central veins at 200-fold magnification. The collagen-positive area ratio (%) was calculated using Image J software based on the images taken, and the normal group (group 1) and the test substance-administered groups (groups 3 and 4) were respectively compared to the sucrose group (group 2).

(8) F4/80 Immunostaining (Inflammation Area %)

With respect to animals of 8 weeks of age at scheduled necropsy, the left outer lobe of the liver was embedded in a CRYO DISH filled with O. C. T. compound, immediately frozen with liquid nitrogen, and preserved at $-80°$ C. for F4/80 immunostaining.

Using a section that was subjected to F4/80 antibody staining according to a conventional method, images of 5 fields of vision per section were taken in a field of vision centered on central veins at 200-fold magnification. The F4/80-positive area ratio (%) was calculated using Image J software based on the images taken, and the normal group (group 1) and the test substance-administered groups (groups 3 and 4) were respectively compared to the sucrose group (group 2).

(9) Result of Disease State Confirmation at 5 Weeks of Age

The result of calculation of fat accumulation area % by oil red staining is shown in Table 6. Since a significant increase in fat accumulation area % was observed in NASH mice (group S2) relative to normal mice (group S1), development of fatty liver in group S2 was confirmed.

TABLE 6

Result of Oil Red staining

|  | Fat accumulation area % | Significant difference |
|---|---|---|
| Group S1 | 0.4 ± 0.5 | Yes |
| Group S2 | 37.5 ± 8.2 | |

* The numerical value indicates mean ± standard deviation.
* The significant difference was determined by testing difference in mean value between group S1 and group S2 by the Student-t test. The presence or absence of a significant difference is shown at 5% level of significance.

(10) Result of Improvement in Fatty Liver at 8 Weeks of Age

The result of oil red staining (calculation of fat accumulation area %) is shown in Table 7. In the sucrose group, a significant difference was not observed at 8 weeks of age (group 2) in comparison with 5 weeks of age (group S2), indicating no improving effect on fatty liver. In the low-dose maltitol group, the value of fat accumulation area was significantly low at 8 weeks of age (group 3) when compared with 5 weeks of age (group S2), and thus an improving effect on fatty liver was observed. In the high-dose maltitol group, the value of fat accumulation area was significantly low at 8 weeks of age (group 4) compared with 5 weeks of age (group S2), and thus an improving effect on fatty liver was observed.

TABLE 7

Result of Oil Red staining (Fat accumulation area %)

| Five weeks of age | | Eight weeks of age | | Significant difference |
|---|---|---|---|---|
| Group S1 | 0.4 ± 0.5 | Group 1 | 0.1 ± 0.2 | |
| | | Group 2 | 34.7 ± 8.4 | No |
| Group S2 | 37.5 ± 8.2 | Group 3 | 32.7 ± 7.6 | Yes |
| | | Group 4 | 28.6 ± 5.5 | Yes |

* The numerical value indicates mean ± standard deviation.
* The significant difference was determined by testing difference in mean value between 5 weeks of age and 8 weeks of age in each group by the Student-t test. The presence or absence of a significant difference is shown at 5% level of significance.

(11) Result of Inhibition of Hepatic Fibrosis at 8 Weeks of Age

The result of Sirius Red staining (calculation of fibrosis area %) is shown in Table 8. The sucrose group (group 2) showed a significant high value in comparison with the normal group (group 1). When compared with the sucrose group (group 2), no significant difference was observed in the low-dose maltitol group (group 3) and the high-dose maltitol group (group 4), but the values in groups 3 and 4 showed a tendency to be low. From the above results, inhibitory effect on fibrosis in the liver tissue was suggested in the low-dose maltitol group (group 3) and the high-dose maltitol group (group 4).

TABLE 8

Result of Sirius Red staining

|  | Fibrosis area % | Significant difference |
|---|---|---|
| Group 1 | 0.27 ± 0.07 | Yes |
| Group 2 | 1.09 ± 0.23 | |
| Group 3 | 0.89 ± 0.15 | Tendency to be different |
| Group 4 | 0.86 ± 0.27 | Tendency to be different |

* The numerical value indicates mean ± standard deviation.
* The significant difference was determined by testing the differences between the normal group (group 1) and the sucrose group (group 2) and between the test substance-administered groups (groups 3 and 4) and the sucrose group (group 2) by Bonferroni method. The presence or absence of a significant difference is shown at 5% level of significance, and the presence or absence of "tendency to be different" is shown at 10% level of significance.

(12) Result of Inhibition of Hepatic Inflammation at 8 Weeks of Age

The result of F4/80 immunostaining (calculation of inflammation area %) is shown in Table 9. The sucrose group (group 2) showed a significant high value in comparison with the normal group (group 1). When compared with the sucrose group (group 2), no significant difference was observed in the high-dose maltitol group (group 4), but the value in group 4 showed a tendency to be low. No significant difference was observed in the low-dose maltitol group (group 3) when compared with the sucrose group (group 2). From the above results, anti-inflammatory effect in the liver tissue was suggested in the high-dose maltitol group (group 4).

TABLE 9

Result of F4/80 Immunostaining

|  | Inflammation area % | Significant difference |
|---|---|---|
| Group 1 | 1.81 ± 0.52 | Yes |
| Group 2 | 3.28 ± 0.95 | |
| Group 3 | 3.04 ± 1.55 | No |
| Group 4 | 2.46 ± 0.44 | Tendency to be different |

* The numerical value indicates mean ± standard deviation.
* The significant difference was determined by testing the differences between the normal group (group 1) and the sucrose group (group 2) and between the test substance-administered groups (groups 3 and 4) and the sucrose group (group 2) by Bonferroni method. The presence or absence of a significant difference is shown at 5% level of significance, and the presence or absence of "tendency to be different" is shown at 10% level of significance.

Example 1

Powder

The raw materials shown in Table 10 were mixed to prepare powders. The powder is one embodiment of liver function-improving agent, fat accumulation inhibitor or a medicament for the prevention/treatment of hepatic dysfunction of the present invention.

TABLE 10

Formulation of powders

| Raw materials | Amount |
|---|---|
| Maltitol | 90 g |
| Lactose | 10 g |

Example 2

Tablet

The raw materials shown in Table 11 were mixed and then direct compression was performed under tableting conditions of punch (φ 8 mm, R 12 mm), 150 to 200 mg weight per tablet, rotation speed of a rotary table of 12 rpm, and compression pressure for tableting of 4 kN, using a continuous tableting press machine (Piccola B-10, manufactured by RIVA Ltd.) to produce tablets. The tablet is one embodiment of liver function-improving agent, fat accumulation inhibitor, or a medicament for the prevention/treatment of hepatic dysfunction of the present invention.

TABLE 11

Formulation of tablet

| Raw materials | Amount |
| --- | --- |
| Maltitol | 94 g |
| Dextrin | 5 g |
| Calcium stearate | 1 g |

Example 3

Liquids and Solutions for Oral Administration

Raw materials listed in Table 12 were dissolved in 500 ml of distilled water to produce liquid and solution for oral administration. The liquid and solution for oral administration is one embodiment of liver function-improving agent, fat accumulation inhibitor, or a medicament for the prevention/treatment of hepatic dysfunction of the present invention.

TABLE 12

Formulation of liquids and solutions for oral administration

| Raw materials | Amount |
| --- | --- |
| Citric acid | 0.3 g |
| Vitamin B1 (thiamine hydrochloride) | 0.05 g |

TABLE 12-continued

Formulation of liquids and solutions for oral administration

| Raw materials | Amount |
| --- | --- |
| Vitamin C (L-ascorbic acid) | 0.06 g |
| Sodium chloride | 0.1 g |
| Isomerized sugar | 10 g |
| Maltitol | 8 g |

What is claimed is:

1. A method of treating hepatic dysfunction due to non-alcoholic fatty liver or non-alcoholic steatohepatitis, which comprises administering an effective amount of maltitol to a subject in need of the treatment of hepatic dysfunction.

2. The method according to claim 1, wherein the treatment of hepatic dysfunction is achieved through inhibition of fat accumulation in the liver, inhibition of hepatic fibrosis, and/or inhibition of hepatic inflammation.

3. The method according to claim 1, wherein the maltitol is administered as a sole active ingredient.

4. The method according to claim 1, wherein the maltitol is administered in the form of solution.

5. The method according to claim 1, wherein the maltitol is administered in the form of food or drink to which the maltitol has been added.

6. A method of inhibiting fat accumulation in the liver of a subject, which comprises administering an effective amount of maltitol to the subject, wherein the subject suffers from non-alcoholic fatty liver or non-alcoholic steatohepatitis.

7. The method according to claim 6, wherein the maltitol is administered as a sole active ingredient.

8. The method according to claim 6, wherein the maltitol is in the form of solution.

9. The method according to claim 6, wherein the maltitol is administered in the form of food or drink to which the maltitol has been added.

* * * * *